United States Patent [19]

Walser

[11] Patent Number: 5,354,771

[45] Date of Patent: Oct. 11, 1994

[54] METHODS FOR TREATMENT OF SEPSIS USING BRANCH CHAIN AMINO ACIDS

[75] Inventor: MacKenzie Walser, Ruxton, Md.

[73] Assignee: The Johns Hopkins University, Baltimore, Md.

[21] Appl. No.: 82,144

[22] Filed: Jun. 24, 1993

Related U.S. Application Data

[63] Continuation of Ser. No. 769,994, Sep. 30, 1991, abandoned.

[51] Int. Cl.$^5$ .................... A61K 31/415; A61K 31/19; A61K 31/195; A61K 31/04
[52] U.S. Cl. .................................... 514/400; 514/557; 514/561; 514/610; 514/921
[58] Field of Search ............... 514/557, 561, 921, 610, 514/400

[56] References Cited

PUBLICATIONS

Nachbauer et al., "Infusion of branched-chain-enriched amino solutions in sepsis", CA 100:61408u, 1984.
Andreoli et al., "Role of glutathione in protecting endothelial cells against hydrogen peroxide oxidant injury", J. Lab Clin. Med., 108(3):190–198, 1986.
Bower et al., Ann. Surg., 203:13–20 (1986).
Hasselgren et al., J. of Parenteral and Enteral Nutrition, 12:244–249 (1988).
U. Andrae et al., "Pyruvate and Related α-Ketoacids Protect Mammalian Cells in Culture Against Hydrogen Peroxide-Induced Cytotoxicity", Toxicology Letters, 28, pp. 93–98 (1985).
A. K. Salahudeen et al., "Hydrogen Peroxide-Induced Renal Injury—A Protective Role for Pyruvate in Vitro and In Vivo", J. Clin. Invest., 88, pp. 1886–1893, (1991).
L. Cavallini et al., "The Protective Action of Pyruvate on Recovery of Ischemic Rat Heart: Comparison with Other Oxidizable Substrates", J. Mol. Cell Cardiol., 22, pp. 143–154 (1990).
N. J. Benevenga et al., "Pyruvate Metabolism in the Dairy Calf", J. Dairy Sci., 47, pp. 1124–1126 (1965).
W. W. Shreeve et al., "Metabolism of [2–$^{14}$C] Pyruvate in Normal, Agromegalic and HGH-Treated Human Subjects", Acta Endo., 65, pp. 155–169 (1970).
A. K. Salahudeen et al., "Pyruvate (PYR) Protects Renal Tubular Epithelial Cells Against Hydrogen Peroxide ($H_2O_2$) by Scavenging $H_2O_2$ Through a Nonenzymatic Decarboxylation Reaction", J. Am. Soc. Nephrol., 1, p. 618 (1990).
K. A. Nath et al., "Pyruvate (PYR) Protects Against Hydrogen Peroxide ($H_2O_2$)-Induced Renal Injury in Vitro and in Vivo", J. Am. Soc., Nephrol., 1, p. 637 (1991).

Primary Examiner—Gregory Hook
Attorney, Agent, or Firm—Panitch Schwarze Jacobs & Nadel

[57] ABSTRACT

Methods for treatment of free-radical-mediated tissue injury, particularly sepsis, are provided wherein compositions containing at least one keto analog of a branched-chain amino acid are administered. The composition is administered orally or parenterally, preferably in frequent or continuous dosages. Preferred forms of the keto analogs are their ornithine, arginine, or sodium salts.

7 Claims, No Drawings

METHODS FOR TREATMENT OF SEPSIS USING BRANCH CHAIN AMINO ACIDS

STATEMENT OF GOVERNMENT INTEREST

The invention described herein was made in part in the course of work under a research grant (DK 32009) from the National Institutes of Health.

CROSS-REFERENCE TO RELATED APPLICATION

This application is a continuation of U.S. application Ser. No. 07/769,994, filed Sep. 30, 1991, now abandoned.

FIELD OF THE INVENTION

The present invention relates to therapeutic treatment of animals and humans suffering from free-radical-mediated tissue injury. More particularly, the invention is directed to the oral or parenteral administration to such animals of compositions which alleviate such injury.

BACKGROUND OF THE INVENTION

In recent years, reactive oxygen metabolites have been postulated to be important mediators of immune-mediated, toxic and ischemic renal injury. See Paller, M. S. et al., *Clin. Invest.*, 74:1156–1164 (1984); Shah, S. V. *Kidney Int.*, 35:1093–1106 (1989); Stratta, P. et al., *Contrib. Nephrol.*, 77:132–141 (1990); Stratta, P. et al., *Am. J. Kid. Dis.* 17:33–37 (1991); Guidet, B. et al., *Am. J. Physiol.*, 257:F440–F445 (1989). They also are thought to play a role in endotoxin-induced tissue injury (Demling, R. H. et al., *Arch. Surg.*, 123:1337–1341 (1988)), such as sepsis, as well as in reperfusion injury of heart and brain.

With respect to renal injury, investigators have determined that various antioxidants and free-radical scavengers appear to retard these injuries. Dietary deficiencies of the antioxidants selenium and vitamin E have been shown to greatly aggravate ischemic renal injury See Modi, K. S. et al., *Kidney Int.*, 38:843–850 (1990). Others investigators have shown that probucol, an antioxidant, improves renal function following a release of bilateral ureteral obstruction (Modi, K. S. et al., *Kidney Int.*, 38:843–850 (1990)) and that dimethylthiourea, a hydroxy radical scavenger, reduces proteinuria and renal histopathology in rats with immune complex glomerulonephritis. See Omata, M. *Nippon Jinzo Gakkai Shi*, 32:949–958 (1990).

With respect to the endotoxin-induced tissue injury resulting from sepsis, alpha-tocopherol and other scavengers have been shown to improve survival in rats. See Powell, R. J. et al., *Am. Surg.*, 57:86–88 (1991). In these models, sepsis was induced by cecal ligation and puncture.

Other investigators have shown that reperfusion injury in rat heart can be greatly reduced by addition of pyruvate prior to ischemia. Studies have determined that pyruvate is a free-radical scavenger and can reduce $H_2O_2$ generation by glucose oxidase. Investigators believe that pyruvate acts either through its direct reaction with $H_2O_2$ or by activation of NADPH-dependent peroxide scavenging systems. See Cavallini, L. et al., *J. Mol. Cell Cardiol.*, 22:143–154 (1990).

Various research groups have investigated the role of pyruvate in renal injury treatment. Pyruvate has been found to protect renal LLC-PK cells from peroxide-induced injury. See Salahudeen, A. K. et al., *J. Am. Soc. Neph.*, 1:618 (1990) and Nath, K. A. et al., *J. Am. Soc. Neph.*, 1:637 (1991). Others have determined that pyruvate infusion attenuates markedly the proteinuria caused by intrarenal infusion of $H_2O_2$ and also reduces post-ischemic renal injury. See Cavallini, L. et al. *J. Mol. Cell Cardiol.*, 22:143–154 (1990). Pyruvate is a naturally occurring 2-ketoacid and other similar compounds such as 2-ketobutyrate, 2-ketoglutarate, and 2-ketoadipate have been demonstrated to provide complete protection, at 1 mM, of Chinese Hamster V79 cells against the lethal effects of $H_2O_2$. See Andrae, U. et al., *Ziegler-Skylakakis K. Toxicology Letters*, 28:93–98 (1985).

Arteriosclerosis is another example of a condition in which oxygen free-radical-mediated injury is believed to play a pathogenetic role. Circulating lipids, when oxidized by free radicals, become prone to deposition in the intimal lining of blood vessels, causing arteriosclerosis.

Free radical scavenging compounds have also been found to be protective in experimental models of acute pancreatitis and in a few patients with this disorder. Lipid peroxide levels are also elevated in this condition.

In patients with respiratory distress syndrome, reactive oxygen species may play a role, since increased concentrations of hydrogen peroxide are seen in expired condensate in such patients. Furthermore, plasma antioxidant activity is reduced.

Despite the demonstrated role of pyruvate as a free radical scavenger and its effects on reduction of reperfusion and renal injury, this compound is unlikely to be practical for use in actual treatment. It is known that pyruvate is relatively rapidly metabolized after its uptake. See Shreeve, W. W. et al., *Acta. Endo.*, 65:155–169 (1970); Hartl, W. H. et al., *Beitr. Infusionther.*, 25:389–398 (1990); Benevenga, N. J. et al., *J. Dairy Sci.*, 47:1124–1126 (1965). Moreover, formulations containing pyruvate are usually not practical from a manufacturing and distribution viewpoint because the compound is too unstable. Similar limitations are applicable to the other naturally occurring 2-ketoacids discussed above.

In addition, the long-term toxicity of 2-ketobutyrate and 2-ketoadipate is unknown. Although 2-ketoglutarate, known to be non-toxic, may be useful as an antioxidant, it is known to be less effective than its monocarboxylic acid.

In addition to the problems of efficacy, unknown toxicity and stability discussed above, many antioxidants suffer from the problem that, after combining with oxygen free radicals and thereby becoming oxidized, they accumulate and can in turn promote oxidation of target molecules. Thus, there exists a need for treatments utilizing therapeutic compositions which can slow or stop the progression of disorders characterized by free-radical-mediated injury such as renal tissue injury, sepsis, reperfusion injury, arteriosclerosis, acute pancreatitis, or respiratory distress syndrome. Development of appropriate methods of treatment could lead to slowing or stopping of the progression of chronic renal failure and other disorders characterized by free-radical-mediated injury in animals and humans.

SUMMARY OF THE INVENTION

Accordingly, an object of the present invention is to provide stable antioxidant or antioxidant-inducing compounds in sustained and effective circulating concentrations to treat or prevent free-radical-mediated tissue injury in animals and humans. This and other objects of the present invention, which will be apparent from the detailed description of the present invention provided below, have been met by a method for treatment of free-radical-mediated tissue injury which comprises oral or parenteral administration of a composition comprising at least one of the keto analogs of the branched-chain essential amino acids valine, leucine or isoleucine in an amount effective to stop or reduce free-radical-mediated tissue injury.

DETAILED DESCRIPTION OF THE PREFERRED EMBODIMENTS

The particular embodiments of the composition employed in the method of the present invention utilize keto analogs of three of the essential amino acids. The branched chain essential amino acids are valine, leucine, and isoleucine, and their corresponding alpha-keto analogs are alpha-ketoisovaleric acid, alpha-ketoisocaproic acid, and alpha-keto-beta-methyl-valeric acid. These branched chain ketoacids are commercially available as calcium or sodium salts or salts of the basic amino acids ornithine, lysine, arginine, and histidine. The methods of making the ketoacids are well known in the art, for example, methods of making the ornithine and arginine salts of the branched chain ketoacids are disclosed in U.S. Pat. No. 4,228,099.

The described composition may be given orally as a mixture, for example, as a flavored powder soluble in water or in gelatin capsules, or parenterally in a sterilized isotonic aqueous solution, the keto analogs being most preferably in the form of their ornithine or arginine salts. In another preferred embodiment, the keto analogs are in the form of their sodium or calcium salts. Preferably, to keep circulating ketoacid concentrations elevated, if the composition is given parenterally, the dosage is given by continuous intravenous infusion; if the administration is oral, the dosages are frequent. For continuous intravenous infusion, the sodium salt is preferred. For individuals having a tendency to retain sodium, use of the calcium salt or basic amino acid salts is preferred for oral dosages.

The keto-acid analog of isoleucine exists in two optical isomeric forms; these two forms are interconverted in the body. The keto analog of L-isoleucine, the naturally occurring amino acid, is dextrorotary. When administered, it is racemized in the body. Since the racemic composition of the keto analogs of L-isoleucine is considerably less expensive than the pure dextro form and has been found equally effective for the purposes of the present invention, the use of racemic alpha-keto-beta-methyl-valeric acid has pronounced economic advantages.

The compositions of the method of the present invention comprise at least one of the keto analogs of valine, leucine or isoleucine, but a combination of two or all three of these may be used.

The above compositions are prepared for intravenous administration by first dissolving the sodium or basic amino acid salt of the keto analog in 50 ml of distilled water with the aid of warming and then adding the remaining components of the mixture to the resulting solution. The solutions are sterilized by filtration and tested for sterility and pyrogenicity. The solution is frozen until use. For use, the solution was thawed to room temperature and diluted to 250 ml with sterile, pyrogen-free water.

The isotonic solution produced has a near neutral pH and is satisfactory for intravenous use. The solution is stable for at least six hours at room temperature.

The method of the present invention is useful for the treatment of sepsis, a severe toxic, feverish state resulting from infection with pyogenic microorganisms. Sepsis may or may not be accompanied by septicemia, a condition wherein pathogenic organisms circulate in the blood, causing fever and other symptoms. Septicemia persists as a serious complication of numerous acute infections, as caused by hemolytic streptococci, staphylococci, pneumococci, meningococci, color bacilli and other pathogens. Portals of entry of these pathogens into the blood include the lungs, middle ear, the mastoid process, the skin and the genitourinary tract. Although there are no consistent signs of septicemia, the condition is suspected when, during the course of an infection, a patient develops unusual fever, hemorrhages into the skin (purpura) or joints, symptoms of endocarditis, jaundice and widespread abscesses. Septicemia is sometimes a complication which may occur in patients on hemodialysis. Antibiotics and other antimicrobial drugs are presently the treatment of choice for this condition.

The compounds used in the method of the present invention have been determined to enhance survival of sepsis-affected rats. Also, the compounds have been shown to reduce a measure of oxidant levels in rats with sepsis. Sepsis-affected rats exhibit high levels of malondialdehyde, an indicator of body oxidant levels. Administration of BCKAs to these rats resulted in a decrease of malondialdehyde concentration into the normal range.

Presently, the mechanism of action of these effects is speculative. Since it is known that BCKA are potent inhibitors of pyruvate dehydrogenase and 2-ketoglutarate dehydrogenase (Jackson, R. H. et al., *J. Biol. Chem.*, 258:1857–1865 (1983); Robertson, J. G. et al., *J. Biol. Chem.*, 261:76–81 (1986); Bowden, J. A. et al., *Biochem. Med.*, 4:69–76 (1970)), BCKA may exert protection by augmenting pyruvate levels. Furthermore, BCKAs can themselves serve as antioxidants. Once oxidized, it is known that BCKAs cannot themselves induce further oxidation of target molecules in contrast to many other antioxidant compounds. BCKAs cannot be synthesized in the body from their oxidized counterparts. Alternatively, certain of the keto analogs such as the leucine analog, 2-ketoisocaproate (KIC), which has been shown to affect pyruvate formation and transport in mitochondria (Quattrochi, L. C. et al., *Biochem. Biophys. Res. Comm.*, 109:950–957 (1982); Halestrap, A. P. et al., *Biochim. Biophys Acta.*, 367:102–108 (1974)), may contribute directly to increased pyruvate levels.

The invention will now be described with reference to the following specific, non-limiting example:

EXAMPLE

The Effect of 2-ketoisocaproate Infusion in Rats With Sepsis

Sepsis was induced in two groups of seven and eight rats each by cecal ligation and puncture. At the time of cecal ligation and puncture, continuous intravenous infusion of either $NaHCO_3$ or sodium 2-ketoisocaproate (NaKIC) was started, plus complete parenteral nutrition. The infusion rate for $NaHCO_3$ or NaKIC was 18.75 mmol/kg/day and was continued for five days or until death. Five out of eight rats in the control group (NaHCO₃ infusion) died while all seven of the rats in the experimental group (NaKIC infusion) survived. This difference is statistically significant ($p<0.05$).

The method of treatment of the present invention is also thought to be useful for the treatment of other free-radical-mediated disorders such as renal injury, reperfusion injury of heart or brain tissue, arteriosclerosis, acute pancreatitis, or respiratory distress syndrome.

The present invention may be embodied in other specific forms without departing from the spirit or essential attributes thereof and, accordingly, reference should be made to the appended claims, rather than to the foregoing specification, as indicating the scope of the invention.

I claim:

1. A method for treatment of sepsis in a patient in need thereof which comprises orally or parenterally administering to said patient a composition comprising at least one keto analog of a branched-chain essential amino acid selected from the group consisting of valine, leucine, and isoleucine in an amount effective to treat sepsis.

2. The method of claim 1 in form for parenteral administration, the composition being in the form of a sterilized isotonic aqueous solution.

3. The method of claim 1 wherein each of the keto analogs is in the form of its salt, the counterion selected from the group consisting of ornithine, lysine, arginine, histidine, calcium, and sodium.

4. The method of claim 3 wherein the parenteral administration is intravenous and continuous to keep circulating ketoacid levels elevated.

5. The method of claim 4 wherein the counterion is sodium.

6. The method of claim 3 wherein the oral administration is frequent to keep circulating ketoacid levels elevated.

7. The method of claim 6 wherein the counterion is ornithine or arginine.

* * * * *